United States Patent [19]

Stegmann

[11] Patent Number: 5,486,165
[45] Date of Patent: Jan. 23, 1996

[54] METHOD AND APPLIANCE FOR MAINTAINING THE NATURAL INTRAOCULAR PRESSURE

[76] Inventor: Robert Stegmann, 88, Copselaine, Lynnwood Glen, Pretoria, 0181, South Africa

[21] Appl. No.: 181,174

[22] Filed: Jan. 13, 1994

Related U.S. Application Data

[63] Continuation of Ser. No. 860629, Mar. 30, 1992, Pat. No. 5,360,399.

[30] Foreign Application Priority Data

Jan. 10, 1992 [CH] Switzerland .................. 062/92

[51] Int. Cl.[6] .................................................. A61M 5/00
[52] U.S. Cl. .................................. 609/294; 604/8
[58] Field of Search ................ 604/8, 9, 10, 265, 604/266, 294, 48, 51, 54; 623/4

[56] References Cited

U.S. PATENT DOCUMENTS

| | | |
|---|---|---|
| 3,915,172 | 10/1975 | Wichterle et al. ................... 604/8 |
| 4,521,210 | 6/1985 | Wong ................................. 604/8 |
| 4,586,921 | 5/1986 | Berson . | 
| 4,722,274 | 2/1988 | Schocket ........................... 604/8 |
| 4,729,761 | 3/1988 | White ................................ 604/8 |
| 4,750,901 | 6/1988 | Molteno ............................ 604/8 |
| 4,759,746 | 7/1988 | Straus . |
| 4,801,297 | 1/1989 | Mueller ...................... 604/264 X |
| 4,826,478 | 5/1989 | Schocket ........................... 604/8 |
| 4,846,172 | 7/1989 | Berlin . |
| 4,936,825 | 6/1990 | Ungerleider ....................... 604/8 |
| 5,041,101 | 8/1991 | Seder et al. ................ 604/264 X |

FOREIGN PATENT DOCUMENTS

| | | |
|---|---|---|
| 0348146 | 12/1989 | European Pat. Off. . |
| 2466994 | 10/1979 | France . |

OTHER PUBLICATIONS

Section PQ. Week 42, Nov. 25, 1981 Derwent Publ., London, GB, (Omsk Med. Inst.).
Section PQ. Week 9232, Derwent Publ., London, GB, (Eye Disease Res. Inst.).
Section PQ, Week 9109, Derwent Publ., London, GB, Class P (Cherednichenko V.I.).

*Primary Examiner*—Sam Rimell
*Attorney, Agent, or Firm*—Henry M. Feiereisen

[57] ABSTRACT

A method and an appliance for carrying out the method, by means of which the necessary outflow of the aqueous humour which is continuously being renewed in the eye is ensured, and thus the natural intraocular pressure is maintained, are proposed. For the treatment, the sclera (13) undergoes operative lamellar incision for partial exposure of the canal of Schlemm (15), and the portion (13') which is opened out is held by means which are not depicted. A medium is introduced into the canal of Schlemm (15) by means of a tube (20) which is introduced into the circular canal of Schlemm (15), by which means the upstream trabecular tissue (15') is hydraulically expanded and traumatically opened at several points (15") and, at the same time, the points (15") are wetted by the highly viscous medium.

13 Claims, 2 Drawing Sheets

METHOD AND APPLIANCE FOR MAINTAINING THE NATURAL INTRAOCULAR PRESSURE

This is a continuation of application Ser. No. 07/860,629, filed Mar. 30, 1992, now U.S. Pat. No. 5,360,399.

BACKGROUND OF THE INVENTION

1. Field of the Invention

The invention relates to a method and to an apparatus for maintaining a constant pressure, which depends on the aqueous humour, inside the eye of an organism, in which the aqueous humour circulating from the posterior chamber to the anterior chamber is removed via the circular canal of Schlemm and via the upstream trabecular tissue.

2. Discussion of Prior Art

For perfect functioning of the eye it is necessary, inter alia, for the pressure of the aqueous humour which is continuously being renewed and circulating between the posterior chamber and the anterior chamber to be balanced in such a way that the outflow and inflow of the aqueous humour are the same, and the outflow of the aqueous humour via the trabecular tissue upstream of the Schlemm's canal is ensured.

Disturbances of the outflow of aqueous humour may occur, for example, when the filtration angle constricts the access to Schlemm's canal in the form of slit, or else when there are pathological changes, which prevent the passage of the aqueous humour, in the trabecular tissue upstream of the Schlemm's canal. If the outflow of the aqueous humour is less than its inflow, the pressure inside the eye increases, which produces the visual disturbance which is known under the name "glaucoma" and often leads to blindness.

Pharmaceutical and surgical methods are known for the treatment of a pathological Schlemm's canal which prevents pressure equalisation, and of the trabecular tissue. The generally known pharmaceutical method may lead to unwanted, troublesome side effects in the patient. The method which opens the canal of Schlemm and the trabecular tissue and is performed surgically or with a laser has not led to the required success in the long term either because regeneration of the tissue closes the openings in the trabecular tissue again after a relatively short time.

SUMMARY OF THE INVENTION

The present invention is directed to a method and apparatus for maintaining a constant pressure, which depends on the aqueous humour which circulates from the posterior chamber to the anterior chamber of the eye and is removed via the circular canal of Schlemm and the trabecular tissue, inside the eye of an organism. The method comprises making a lamellar incision of the sclera thereby exposing a section of Schlemm's canal and then injecting a highly viscous medium into the canal for opening the trabecular tissue traumatically by a hydraulic expansion at one or more points and which prevents a hemorrhage thereof.

The object of the invention is thus to indicate a method and an apparatus for carrying out the method, by means of which the outflow of the continuously renewing aqueous humour is ensured.

The method according to the invention is characterised in that a medium which opens the trabecular tissue essentially traumatically by a hydraulic expansion at one or more points and which prevents a haemorrhage is injected by means of a tube introduced into the canal of Schlemm.

The apparatus according to the invention for carrying out the method comprises an injection apparatus and a tube connected thereto and is characterised in that the tube is designed in the form of an arc of a circle and is provided at least on the inside of the arc with orifices which are arranged at intervals from one another.

Further features of the invention are evident from the following description in conjunction with the drawing and the other patent claims.

DESCRIPTION OF PREFFERED EMBODIMENTS

Figure 1:
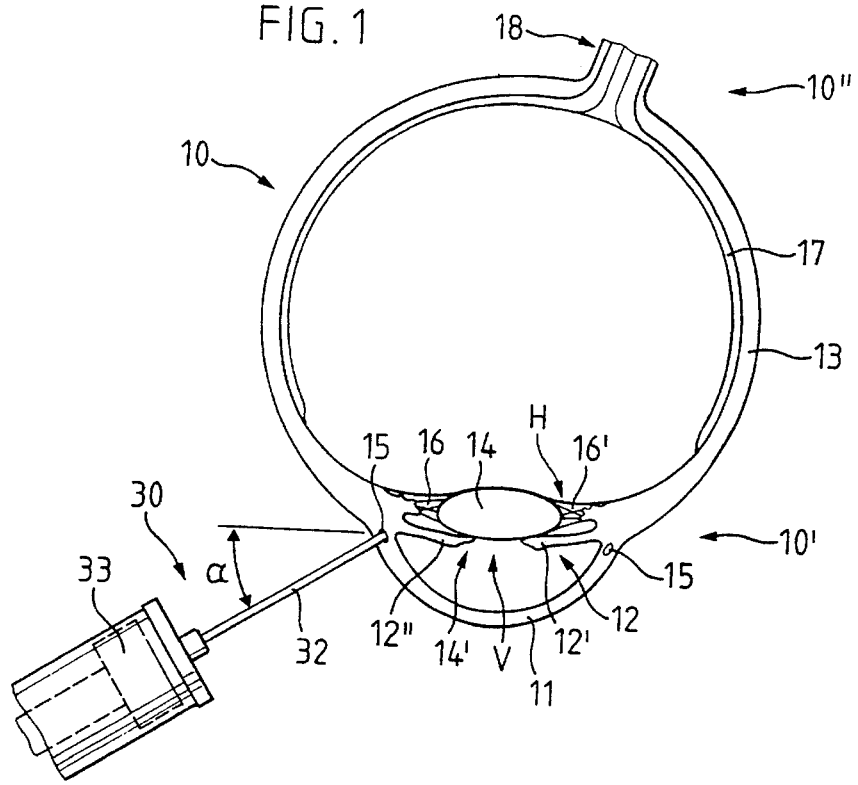
FIG. 1 shows an eye, which is depicted diagrammatically and in section, of an organism with the anterior and posterior section of the eye.

FIG. 1 shows an eye which is depicted in section and is totality labelled with 10, where 10" labels the posterior section of the eye and 10' labels the anterior section of the eye. The aqueous humour is formed in the anterior section 10' of the eye.

Evident in the anterior section 10' of the eye are the cornea 11, the iris 12 with the two regions 12' and 12' the sclera 13, the lens 14 (ocular) with the pupil 14', the ciliary rings 16,16', and the Schlemm's canal 15 (sinus venosus sclearae). The circular canal of Schlemm 15, which is located approximately in the apex of the angle of the junction of the cornea and the sclera 13, runs essentially parallel to the margin of the cornea 11. Also evident are the retina 17 and the optic nerve which is in totality labelled with 18.

Figure 4:
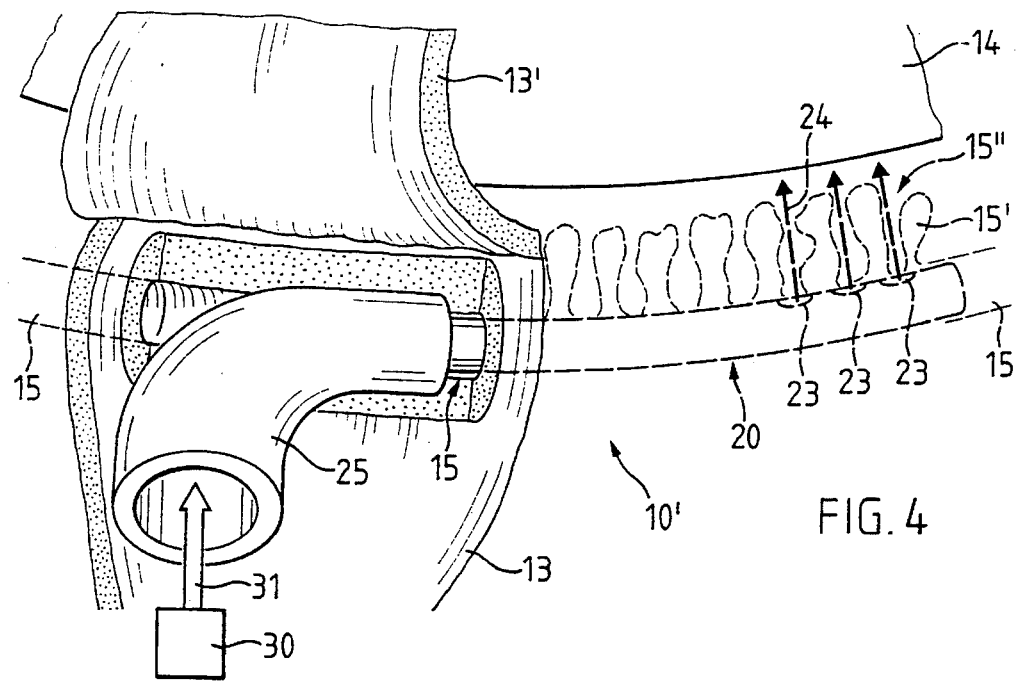
FIG. 4 shows a view of a portion of the eye depicted on a larger scale with a tube introduced into a part of the Schlemm's canal, FIG. 5. shows a portion, which is depicted as first exemplary embodiment and in a sectional view, of the tube, FIG. 6. shows a portion, which is depicted as second exemplary embodiment and in a section view, of the tube.

In a healthy eye, outflow of the aqueous humour which is continuously being renewed and circulating between the posterior chamber H and the anterior chamber V takes place via the Schlemm's canal 15 and via the upstream tissue 15' (trabeculum corneosclerae) which is depicted in FIG. 4 and is provided with opening 15". The outflow and inflow of the aqueous humour are the same in a healthy eye.

In a diseased eye the Schlemm's canal 15 and/or the upstream tissue 15' with the openings 15" and with the canalicular venous network which is not depicted can become closed in such a way that the outflow of the aqueous humour is less than the inflow and thus the pressure inside the eye increases so that the optic nerve 18 is correspondingly pinched. This visual disturbance, which is known under the name "glaucoma" often leads to blindness of the affected eye or of both eyes.

To treat the single diseased eye, a highly viscous medium is injected into Schlemm's canal 15 by means of an injection apparatus 30. The injection apparatus 30 comprises, as depicted diagrammatically in FIG. 1, at least one syringe 33, and a tube which is introduced appropriately into Schlemm's canal 15 and is not depicted in detail in FIG. 1 and which is connected via a supply line 32 to the syringe 33. The syringe 33 is, for example, an exchangeable piston syringe known per se, which can be actuated either manually or else electronically controlled with means which are not depicted.

For the injection of the highly viscous medium, the injection apparatus 30 is arranged with the supply line 32, as depicted in FIG. 1, at an angle α, which is of the order 45°, relative to Schlemm's canal 15.

Figure 2:
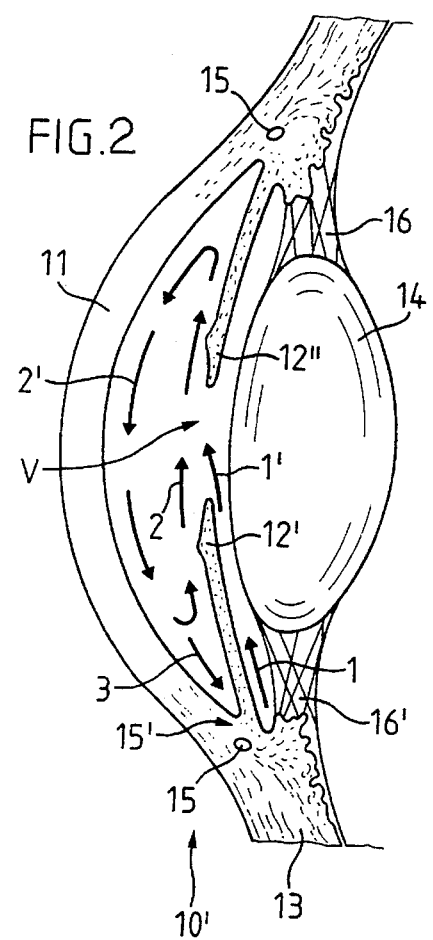
FIG. 2 shows the anterior section of the eye depicted on a larger scale and in section.

The anterior section 10' of the eye 10 is depicted on a larger scale and in section in FIG. 2, and the cornea 11, the two regions 12' and 12" of the iris 12, the sclera 13, the lens 14 with the ciliary rings 16, 16', and the canal of Schlemm 15 are evident. The aqueous humour which is depicted diagrammatically with the arrows 1,1' and 2,2' circulating in the region of the anterior chamber v is supplied in the direction of the arrow 3 to Schlemm's canal 15 and removed from the latter in a manner which is not depicted in detail via the upstream tissue 15' (FIG. 4) and via the canalicular venous network.

Figure 3:
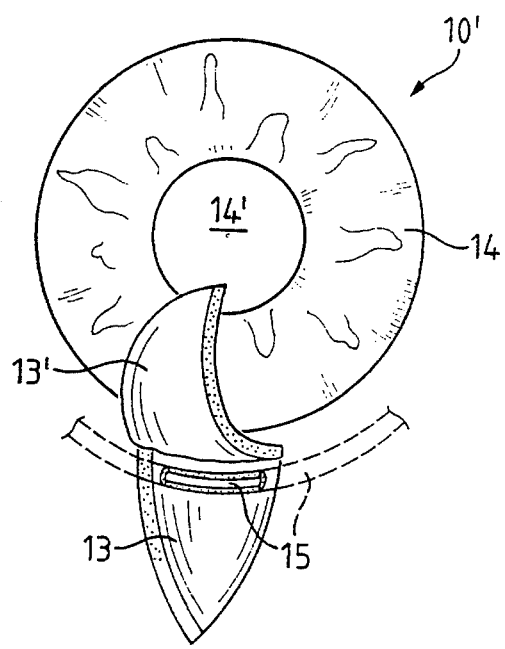
FIG. 3 shows a view of a portion of the eye which is depicted with the sclera incised and opened out, with an exposed portion of the Schlemm's canal.

FIG. 3 shows the anterior section 10' of the eye depicted in view, and the lens 14 with the pupil 14', and the sclera 13 which is partly depicted, are evident. To expose a section of Schlemm's canal 15 which encircles the lens 14, the sclera 13 is subjected to operative lamellar incision, and the outer part is opened out appropriately as a flap-like portion 13'. The opened-out portion 13' of the sclera is in this case held with means which are not depicted.

FIG. 4 depicts on a larger scale the anterior section 10' of the eye with Schlemm's canal 15 which is partly exposed and with the portion 13' of the sclera which is opened out. A tube 20 which is in the form of a small pipe is introduced into the canal of Schlemm 15 and is provided on the surface which faces the upstream tissue 15' with openings 23 which are arranged at intervals from one another. The tube 20 has two or three openings 23, preferably only in the end region, which are arranged in a row. A curved connector 25 is arranged at one end of the tube 20 and is connected in a manner which is not depicted in detail in the form of a coupling to the supply line 32 of the injection apparatus 30 (FIG. 1). The highly viscous medium is injected into Schlemm's canal 15 via the tube 20 by the injection apparatus 30 in the direction shown by the arrow 31.

On injection of the medium, the Schlemm's canal 15, as depicted diagrammatically in FIG. 4, is appropriately hydraulically expanded at the side which has less support and faces the anterior chamber V (FIG. 1,2) in such a way that the canal of Schlemm 15 subsequently bursts at the weakest points in the direction of the arrow 24 and, in this way, forms an opening 15" in the trabecular tissue 15 in each case, where the openings 15" essentially correspond in each case to the opening 23 provided in the tube 20.

In FIG. 4, one portion (on the right), which has been exposed by the incision, of Schlemm's canal 15 is treated by means of the tube 20. Subsequently the other portion of Schlemm's canal 15 is treated by means of a tube 20' which is designed as mirror image and introduced into the other portion (on the left) of the canal of Schlemm 15. The two canal portions are preferably treated successively, with the opposite tube in each case being removed from the canal 15.

Figure 5:
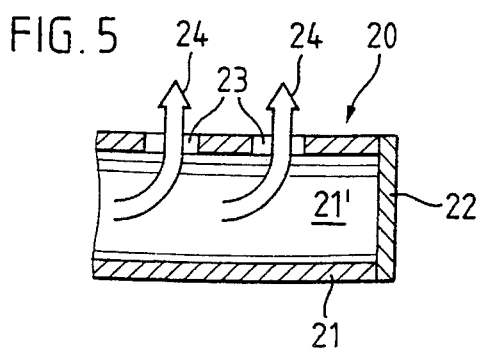

FIG. 5 shows, as first exemplary embodiment a portion of the tube 20 which is depicted in sectional view and an essentially larger scale. The tube 20 which is designed in the form of a small pipe has an external diameter which is suited to the internal diameter of Schlemm's canal 15 and is of the order of about 0.15 mm in size. The tube 20 can be closed with a front plate 22 or the like at one end which is introduced into Schlemm's canal 15 (FIG. 4). Openings 23 are provided on the end of the tube 20 which is introduced into the canal of Schlemm 15 and penetrate through the wall 21 to connect to the interior 21' of the tube 20.

Two to four openings 23 which are connected to the interior 21' are preferably located in the last third of the tube 20 and through which the highly viscous medium, as depicted in FIG. 4, can escape in the direction of the arrow 24 through the trabecular tissue 15'. The openings 23 which are arranged in a row and at intervals from one another can, moreover, have dimensions of equal size or else different sizes.

Figure 6:
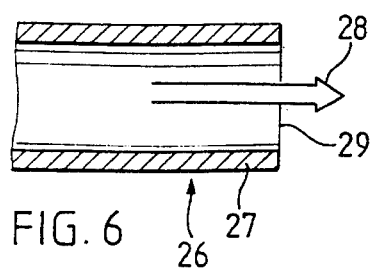

In the second exemplary embodiment depicted in FIG. 6, a tube 26 in the form of a small pipe is provided with a single opening 29 on the front, through which the highly viscous medium is introduced in the direction of arrow 28 into Schlemm's canal 15 (FIG. 4). No further openings are provided in the wall 27 in this exemplary embodiment.

Figure 7:
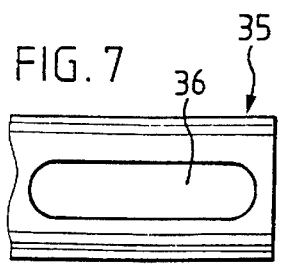
FIG. 7 shows a view of a portion, which is depicted as third exemplary embodiment, of the tube.

FIG. 7 shows, as third exemplary embodiment, a depiction of a view of a portion of a tube 35 which is provided with an opening 36 which is designed as elongate hole and through which the highly viscous medium is introduced into Schlemm's canal 15 (FIG. 4). In a variant which is not depicted in detail, the opening 36 can also be designed as slit extending to the end.

It is pointed out at this juncture that the tube 20, 26 or 35 can in each case be provided in the end region with openings of different designs. For example, the tube 20 which is depicted in FIG. 5 and provided with openings 23 can be provided on the front with an opening 29 in analogy to the tube 26 shown in FIG. 6.

Figure 8:
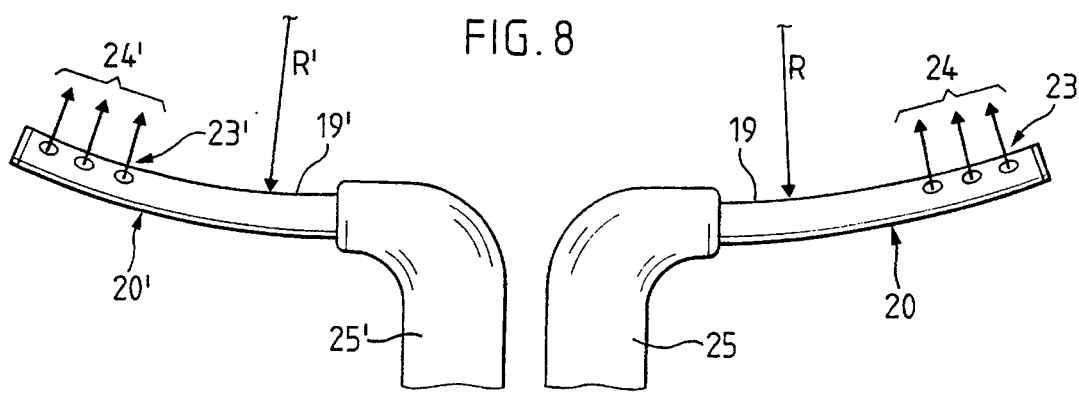
FIG. 8 shows two tubes which are designed as mirror images for the circular canal of Schlemm, each with connectors located thereon for connection to an injection apparatus.

FIG. 8 shows a depiction of a view of two tubes 20 and 20' which are designed as mirror images and which are introduced separately into the canal of Schlemm 15 (FIG. 4) for the treatment, that is to say that, for example, first one tube 20 is introduced and, after the treatment, removed and subsequently the other tube 20' is introduced into Schlemm's canal 15. The single tube 20 or 20' is designed in the form of a curve and has a radius R or R' suited to the essentially circular canal of Schlemm 15. The radius R or R' is of the order of about 12 mm to 14 mm in size. Also evident in FIG. 7 are the openings 23 or 23' arranged at one end of the tube 20 pr 20' in the end region on the inside of the curve 19 or 19', and the connectors 25 or 25', arranged at the other end in each case, for the injection apparatus 30 which is not depicted here. The medium is injected in the direction of the trabecular tissue 15' (FIG. 4) from the opening 23,23' approximately in the direction of the arrow 24,24'.

The tube 20,20',26 or 35 is preferably produced from stainless steel, it likewise being possible to use a suitable plastic.

The medium to be injected in a highly viscous gel by means of which the surfaces of the traumatically produced openings 15" are wetted so that the actual drainage-like function of Schlemm's canal 15 is ensured for a lengthy period even after dissolution of the gel.

The medium to be injected must be physiologically and ophthalmologically tolerated and must not cause any unwanted side effects in Schlemm's canal 15 and in the trabecular tissue 15'. On the one hand, the medium is intended to prevent the bleeding which occurs on traumatic opening of Schlemm's canal 15 and, on the other hand, the wetting of the openings 15' must persist until local tissue union (cell and scar formation) is no longer possible.

A preferred, physiologically and ophthalmologically tolerated medium is, for example, disclosed in U.S. Pat. No. 4,141,973 and U.S. Pat. No. 4,713,448. The known medium is a highly viscous aqueous solution which is supplemented with so-called buffer additives such as phosphates and/or salts.

The medium is, for example, an aqueous solution of the sodium salt of hyaluronic acid, which salt forms a glycosaminoglycan with high molecular weight, the glycosaminoglycan being a chemically modified hyaluronic acid. The molecular weight is preferably of the order of $3.2 \times 10^{-6}$ to $5 \times 10^{-6}$.

It is pointed out at this juncture that it is also possible to use aqueous solutions of lower viscosity. However, in this case it is necessary for the medium to contain ophthalmologically tolerated anticoagulant substances such as, for example, epsilon-aminocaproic acid.

It is also possible to use other ophthalmologically comparable media based on hyaluronic acid, such as, for example, hydroxypropylmethylcellulose, polyacrylamides, mucopolysaccharides, chondroitin sulphate or other types of polysaccharides. It is furthermore possible also to use mixtures of substances such as, for example, hyaluronic acid with chondroitin sulphate or hyaluronic acid with dextran.

While the invention has been particularly shown and described with respect to the preferred embodiments thereof, it should be understood by those skilled in the art that the foregoing and other changes in form and details may be made therein without departing from the spirit and scope of the invention which should be limited only by the scope of the appended claims.

I claim:

1. An apparatus for injecting a highly viscous medium into Schlemm's canal for maintaining a constant pressure of the aqueous humor circulating from the posterior chamber to the anterior chamber of the eye of an organism, said apparatus comprising an injection unit and a tube which has a closed end and is made of biocompatible material, said tube being connected to the injection unit and designed in the form of an arc of a circle defined by a single curvature with a radius in the range of about 12 mm to 14 mm to generally conform to the curvature of the Schlemm's canal, said tube having one end provided on the inside of the arc facing the trabecular tissue with at least one orifice and another end provided with a coupling for connection of the tube to the injection unit for introduction of viscous medium into the Schlemm's canal to thereby hydraulically expand the Schlemm's canal and burst it at one or more points for creating a corresponding number of openings to form a connection between the Schlemm's canal and the trabecular tissue for drainage of aqueous humor.

2. An apparatus according to claim 1, wherein the tube is provided with orifices in a row in an end region of the one end.

3. An apparatus according to claim 1, wherein the tube has at least two to four orifices.

4. An apparatus according to claim 1, wherein the tube has an outer diameter of about 0.15 mm.

5. An apparatus according to claim 1, wherein the tube is provided on the inside of the arc with a plurality of orifices arranged at intervals from one another.

6. An apparatus according to claim 1, wherein the tube has a wall, said orifice being configured in form of a single elongate hole provided in said wall of said tube.

7. An apparatus according to claim 1, wherein the orifice is provided on the front of the tube.

8. An apparatus for maintaining a constant pressure of the aqueous humor circulating from the posterior chamber to the anterior chamber of the eye of an organism, said apparatus comprising an injection unit having means for injecting a viscous gel medium and a tube which is made of biocompatible material and designed in the form of an arc of a circle to generally conform to the curvature of the Schlemm's canal and to allow insertion of the tube in the Schlemm's canal, said tube having one end provided on the inside of the arc facing the trabecular tissue with at least one orifice and another end connected to the injection unit for conducting viscous medium through the tube and the orifice to hydraulically expand the Schlemm's canal and burst it at one or more points so as to form a connection between the Schlemm's canal and the trabecular tissue after removal of the tube for drainage of aqueous humor.

9. An apparatus according to claim 8, wherein the tube is provided with orifices in a row in an end region of the one end.

10. An apparatus according to claim 8, wherein the tube has at least two to four orifices.

11. An apparatus according to claim 8, wherein the tube has a curvature with a radius in the range of 12 mm to 14 mm and having an outer diameter of about 0.15 mm.

12. An apparatus according to claim 8, wherein the tube is provided on the inside of the arc with a plurality of orifices arranged at intervals from one another.

13. An apparatus according to claim 8, wherein the tube has a wall, said orifice being configured in form of a single elongate hole provided in said wall of said tube.

\* \* \* \* \*